United States Patent [19]

Schirmer et al.

[11] Patent Number: 4,518,414

[45] Date of Patent: May 21, 1985

[54] THIADIAZOLE DERIVATIVES AND THEIR USE FOR CONTROLLING UNDESIRABLE PLANT GROWTH

[75] Inventors: Ulrich Schirmer, Heidelberg; Peter Plath, Ludwigshafen; Bruno Wuerzer, Otterstadt, all of Fed. Rep. of Germany

[73] Assignee: BASF Aktiengesellschaft, Fed. Rep. of Germany

[21] Appl. No.: 457,186

[22] Filed: Jan. 11, 1983

[30] Foreign Application Priority Data

Jan. 22, 1982 [DE] Fed. Rep. of Germany ....... 3201861

[51] Int. Cl.³ .................... C07D 285/12; A01N 43/82
[52] U.S. Cl. ......................................... 71/90; 544/63; 544/134; 546/277; 548/139; 548/140
[58] Field of Search ................ 548/139, 140; 546/207; 544/134; 71/90

[56] References Cited

U.S. PATENT DOCUMENTS

| | | | |
|---|---|---|---|
| 2,805,226 | 9/1957 | Young et al. ........................ | 548/139 |
| 4,066,436 | 1/1978 | Kirkpatrick ......................... | 548/139 |
| 4,195,181 | 3/1980 | Metzger et al. ..................... | 71/90 |
| 4,252,961 | 2/1981 | Lavanish ............................. | 548/139 |
| 4,264,353 | 4/1981 | Lavanish ............................. | 548/139 |
| 4,268,675 | 5/1981 | Lavanish ............................. | 548/139 |

FOREIGN PATENT DOCUMENTS

| | | |
|---|---|---|
| 765930 | 6/1972 | Belgium . |
| 1323227 | 7/1973 | United Kingdom . |
| 1380977 | 1/1975 | United Kingdom . |

*Primary Examiner*—Robert Gerstl
*Attorney, Agent, or Firm*—Keil & Weinkauf

[57] ABSTRACT

Thiadiazole derivatives of the formula

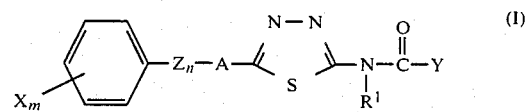

where $R^1$, A, X, Y, Z, m and n have the meanings given in the description, are used for controlling undesirable plant growth.

11 Claims, No Drawings

THIADIAZOLE DERIVATIVES AND THEIR USE FOR CONTROLLING UNDESIRABLE PLANT GROWTH

The present invention relates to thiadiazole derivatives, herbicides which contain these compounds as active ingredients, and a method of controlling undesirable plant growth with these compounds.

It is known that 3-(5-tert.-butyl-1,3,4-thiadiazol-2-yl)-1,3-dimethylurea possesses herbicidal activity (Belgian Pat. No. 765,930) and is used in particular as a nonselective herbicide.

We have found that thiadiazole derivatives of the formula

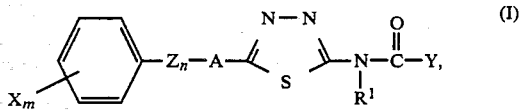

where $R^1$ is hydrogen or $C_1$–$C_4$-alkyl, A is an alkylene chain of 1 to 8 carbon atoms which is unsubstituted or substituted by $C_1$–$C_4$-alkyl, X is hydrogen, halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-alkylsulfonyl, $C_3$–$C_6$-cycloalkyl, phenyl, or unsubstituted or halogen-substituted aryloxy, m is 0, 1, 2, 3 or 4, Y is $C_1$–$C_4$-alkyl, $C_3$–$C_6$-cycloalkyl, $C_1$–$C_4$-alkoxy, $C_1$–$C_4$-alkylthio or $NR^2R^3$, where $R^2$ and $R^3$ independently of one another are each hydrogen, $C_1$–$C_4$-alkyl, $C_2$–$C_4$-alkenyl, $C_2$–$C_4$-alkynyl, $C_1$–$C_4$-alkoxy, $C_2$–$C_5$-alkoxyalkyl or $C_3$–$C_6$-cycloalkyl, or $R^2$ and $R^3$ together form an alkylene chain of 3 to 7 carbon atoms which is unsubstituted or methyl-substituted and may or may not be interrupted by oxygen, Z is oxygen or sulfur and n is 0 or 1, and where the radical

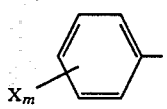

may be replaced by naphthyl which is unsubstituted or substituted by halogen, $C_1$–$C_4$-alkyl or $C_1$–$C_4$-alkoxy, exhibit a good herbicidal action in the case of a large number of important undesirable plants, and are well tolerated by various crop plants.

In formula I, $R^1$ is hydrogen or $C_1$–$C_4$-alkyl, eg. methyl, ethyl, i-propyl or t-butyl, A is an alkylene chain of 1 to 8 carbon atoms which is unsubstituted or substituted by $C_1$–$C_4$-alkyl, eg. methylene, methylmethylene, ethylene, methylethylene, dimethylmethylene, dimethylethylene, propylene, methylpropylene, ethylmethylene, butylene, pentylene, hexylene, heptylene, methylbutylene or octylene, X is hydrogen, halogen, eg. chlorine, bromine, fluorine or iodine, cyano, nitro, $C_1$–$C_4$-alkyl, $C_1$–$C_4$-alkoxy, $C_1$–$C_4$-alkylthio, $C_1$–$C_4$-haloalkyl, $C_1$–$C_4$-haloalkoxy, $C_1$–$C_4$-alkylsulfonyl, $C_3$–$C_6$-cycloalkyl, phenyl or unsubstituted or halogen-substituted aryloxy, such as unsubstituted or halogen-substituted phenoxy, eg. methyl, ethyl, t-butyl, methoxy, ethoxy, t-butoxy, methylthio, ethylthio, n-butylthio, trifluoromethyl, difluoromethoxy, 1,1,2-trifluoro-2-chloroethoxy, methylsulfonyl, cyclopentyl, cyclohexyl, phenoxy, 4-chlorophenoxy or 2,4-dichlorophenoxy, Y is $C_1$–$C_4$-alkyl, eg. methyl, ethyl, t-butyl or s-butyl, $C_3$–$C_6$-cycloalkyl, eg. cyclopropyl, $C_1$–$C_4$-alkoxy, eg. methoxy, ethoxy or isopropoxy, $C_1$–$C_4$-alkylthio, eg. methylthio or ethylthio, or $NR^2R^3$, where $R^2$ and $R^3$ independently of one another are each hydrogen, $C_1$–$C_4$-alkyl, $C_2$–$C_4$-alkenyl, $C_2$–$C_4$-alkynyl, $C_1$–$C_4$-alkoxy, $C_2$–$C_5$-alkoxyalkyl or $C_3$–$C_6$-cycloalkyl, eg. methyl, ethyl, i-propyl, n-butyl, t-butyl, allyl, propargyl, 1-methylprop-2-ynyl, methoxy, ethoxy, n-propoxy, methoxyethyl, cyclopropyl or cyclopentyl, or $R^2$ and $R^3$ together furthermore may form an alkylene chain of 3 to 7 carbon atoms which is unsubstituted or substituted by methyl and may or may not be interrupted by oxygen, eg. propylene, pentylene or hexylene, 1,4-dimethylbutylene, 3-oxapentylene, 2-oxapentylene or 2-oxabutylene, and Z is oxygen or sulfur. The radical

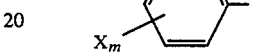

in formula I may furthermore be replaced by α- or β-naphthyl which is unsubstituted or substituted by halogen, $C_1$–$C_4$-alkyl or $C_1$–$C_4$-alkoxy, eg. α-naphthyl, β-naphthyl, 4-chloro-α-naphthyl, 7-methoxy-α-naphthyl or 2-methyl-α-naphthyl.

Preferred thiadiazole derivatives of the formula I are those in which $R^1$ is $C_1$–$C_4$-alkyl, in particular methyl, and Y is $NR^2R^3$, where $R^2$ is hydrogen and $R^3$ is $C_1$–$C_4$-alkyl, in particular methyl.

The thiadiazole derivatives of the formula I are obtained by a process wherein an aminothiadiazole of the formula

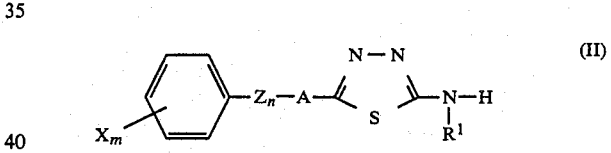

where $R^1$, A, X, Z, m and n have the above meanings, is reacted with an acid chloride of the formula

Y—CO—Hal  (III)

where Y has the above meanings and Hal is halogen, eg. chlorine or bromine.

The reaction is carried out in the presence or absence of an inert organic solvent, examples of suitable solvents being hydrocarbons, eg. naphtha, gasoline, toluene, pentane and cyclohexane, halohydrocarbons, eg. methylene chloride, chloroform, dichloroethane, chlorobenzene and o-, m- and p-dichlorobenzene, nitrohydrocarbons, eg. nitrobenzene and nitromethane, nitriles, eg. acetonitrile, butyronitrile and benzonitrile, ethers, eg. diethyl ether, tetrahydrofuran and dioxane, esters, eg. ethyl acetate and methyl propionate, ketones, eg. acetone and methyl ethyl ketone, and amides, eg. dimethylformamide and formamide, as well as mixtures of such solvents. The amount of solvent is from 100 to 5,000% by weight, based on the aminothiadiazole of the formula II.

Advantageously, the reaction is carried out in the presence of a conventional acid acceptor, suitable examples being alkali metal hydroxides, alkali metal carbonates, alkali metal bicarbonates, alkaline earth metal hydroxides, alkaline earth metal carbonates, alkaline earth metal bicarbonates, alkaline earth metal oxides and amines, eg. sodium bicarbonate, potassium carbonate, triethylamine, tributylamine, pyridine, N,N-dimethylaniline, N,N-dimethyl-N-cyclohexylamine and quinoline. From 1 to 4 moles of acid acceptor are employed per mole of the compound of the formula III.

The starting materials of the formulae II and III are preferably employed in equimolar amounts. The reaction is carried out at from −20° to +150° C., preferably from 20° to 80° C.

Furthermore, thiadiazole derivatives of the formula I where $R^1$, A, X, Z, m and n have the above meanings and Y is $NR^2R^3$, where $R^2$ is hydrogen and $R^3$ has the above meanings, are obtained by a process wherein an aminothiadiazole of the formula

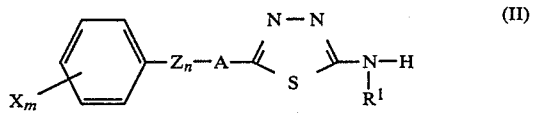

where $R^1$, A, X, Z, m and n have the above meanings, is reacted with an isocyanate of the formula $$R^3\text{—NCO} \qquad (IV)$$

where $R^3$ has the above meanings.

This reaction is carried out in the presence or absence of a catalyst conventionally used for isocyanate reactions, for example a tertiary amine, such as triethylamine or 1,4-diazabicyclo[2,2,2]octane, a nitrogen-containing heterocyclic compound, such as pyridine or 1,2-dimethylimidazole, or an organic tin compound, such as dibutyl-tin diacetate or dimethyl-tin dichloride, and in the presence or absence of a solvent which is inert under the reaction conditions, for example a hydrocarbon, such as naphtha, gasoline, toluene, pentane or cyclohexane, a halohydrocarbon, such as methylene chloride, chloroform, dichloroethane, chlorobenzene or o-, m- or p-dichlorobenzene, a nitrohydrocarbon, such as nitrobenzene or nitromethane, a nitrile, such as acetonitrile, butyronitrile or benzonitrile, an ether, such as diethyl ether, tetrahydrofurane or dioxane, an ester, such as ethyl acetate or methyl propionate, a ketone, such as acetone or methyl ethyl ketone, or an amide, such as dimethylformamide or formamide (Houben-Weyl, Methoden der organ. Chemie, Vol. VIII, page 132, Georg Thieme-Verlag, Stuttgart, 4th edition, 1952). The amount of catalyst is from 0.1 to 5 mole % and the amount of solvent is from 100 to 10,000% by weight, the percentages being based in each case on the aminothiadiazole of the formula II.

The reaction can be carried out at from −20° to 150° C., preferably from 0° to 100° C.

Aminothiadiazoles of the formula

where $R^1$ is $C_1$–$C_4$-alkyl, A is an alkylene chain of 1 to 8 carbon atoms which is unsubstituted or substituted by methyl, X is hydrogen, halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-alkylsulfonyl, $C_3$–$C_6$-cycloalkyl, phenyl or aryloxy, m is 0, 1, 2, 3 or 4, Z is oxygen or sulfur and n is 0 or 1, and where the radical

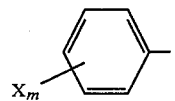

can be replaced by naphthyl which is unsubstituted or substituted by halogen, $C_1$–$C_4$-alkyl or $C_1$–$C_4$-alkoxy, are obtained by a process wherein a carboxylic acid of the formula

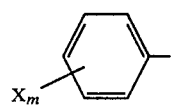

where A, X, Z, m and n have the above meanings, is reacted with a thiosemicarbazide of the formula $$H_2N\text{—NH—CS—NHR}^1 \qquad (VI)$$

where $R^1$ has the above meanings.

This reaction can be carried out in the presence of a solvent which is inert under the reaction conditions, suitable examples being hydrocarbons, eg. gasoline, toluene and cyclohexane, halohydrocarbons, eg. methylene chloride, chlorobenzene and dichlorobenzene, and ethers, eg. tetrahydrofuran and dioxane. The reaction temperature is from 0° to 150° C., preferably from 40° to 120° C., and it is advantageous to employ an agent which eliminates water, eg. sulfuric acid, hydrofluoric acid, polyphosphoric acid, phosphorus pentoxide or phosphorus oxychloride.

The Example illustrates the synthesis of the aminothiadiazoles.

6 g of phosphorus oxychloride were added dropwise, in the course of half an hour, to 25 g of ω-4-chlorophenoxybutyric acid, 10.6 g of thiosemicarbazide and 250 g of dioxane, at 90° C., after which the mixture was stirred under reflux for 1 hour, cooled and then evaporated down in a rotary evaporator. The residue was stirred with water and sufficient sodium hydroxide solution to bring the pH to about 10. The precipitated crystals were filtered off under suction and dried, and the white substance thus obtained had a melting point of 188°–190° C. and was of the following formula:

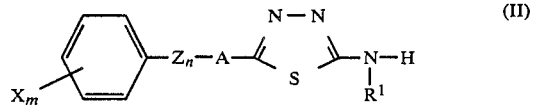

The following aminothiadiazoles of the formula II were prepared or may be prepared in a similar manner:

| A | $Z_n$ | $X_m$ | $R^1$ | Mp [°C.] |
|---|---|---|---|---|
| —$CH_2$— | O | 4-Cl | $CH_3$ | 138–140 |
| " | O | 4-Cl | H | 215–217 |
| " | — | 4-phenyl | $CH_3$ | 165–167 |
| " | — | 4-phenyl | H | 229– |

| A | $Z_n$ | $X_m$ | $R^1$ | Mp [°C] |
|---|---|---|---|---|
| " | — | H | CH$_3$ | 231 102–104 |
| " | — | H | H | 178–180 |
| —(CH$_2$)$_3$— | O | 4-Cl | CH$_3$ | 105–107 |
| " | O | 4-Cl | H | 188–190 |
| " | — | H | CH$_3$ | 56–58 |
| " | — | H | H | 180–182 |
| —(CH$_2$)$_4$— | O | 4-Cl | CH$_3$ | 83–85 |
| " | O | 4-Cl | H | 157–160 |
| —(CH$_2$)$_2$— | O | 4-t.-C$_4$H$_9$ | CH$_3$ | 114–116 |
| —(CH$_2$)$_3$— | O | 4-t.-C$_4$H$_9$ | H | 194–196 |
| —(CH$_2$)$_3$— | O | H | CH$_3$ | 88–90 |
| " | O | H | H | |
| " | O | 4-C$_2$H$_5$ | H | 178–180 |
| " | O | 4-CH$_3$O | H | 186–188 |
| " | O | 4-Br | H | 200–202 |
| " | O | 3-F | H | 172–174 |
| " | O | 2-Cl | H | 184–186 |
| —(CH$_2$)$_3$— | O | 3,4-Cl$_2$ | H | 164–166 |
| " | O | 3,5-Cl$_2$ | H | 171–172 |
| " | O | 4-CN | H | 154–156 |
| —(CH$_2$)$_2$— | O | 4-Cl | CH$_3$ | |
| " | O | 4-Cl | H | |
| —(CH$_2$)$_3$— | O | 3-CH$_3$ | H | 180–182 |
| " | O | 3-CH$_3$ | CH$_3$ | 108–110 |
| " | O | 3-Cl | " | 85–86 |
| " | O | 4-CH$_3$ | " | 115–117 |
| " | O | 2-Cl | " | 68–70 |
| " | O | 4-NO$_2$ | " | 135–137 |
| " | O | 4-CN | " | 119–121 |
| " | O | 3-NO$_2$ | " | |
| " | S | H | " | |
| " | S | 4-Cl | " | |
| " | O | 4-Br | " | 138–140 |
| " | O | 4-SCH$_3$ | " | |
| " | O | 4-SO$_2$CH$_3$ | " | |
| " | O | 4-OCH$_3$ | " | 110–112 |
| " | O | 4-t-C$_4$H$_9$ | " | 107–109 |
| " | O | 4-C$_2$H$_5$ | " | 100–102 |
| " | O | 4-CF$_3$ | " | |
| " | O | 3-CF$_3$ | " | 78–80 |
| " | O | 3,5-Cl$_2$ | " | 89–90 |
| " | O | 3,4-Cl$_2$ | " | 103–105 |
| " | O | 4-C$_5$H$_9$ | " | |
| " | O | 4-C$_6$H$_{11}$ | " | |
| " | O | 4-(4'-chlorophenoxy) | " | |
| " | O | 4-(2',4'-dichlorophenoxy) | " | |
| " | O | 4-phenoxy | " | |
| " | O | 3-OC$_2$H$_5$ | " | |
| " | O | 2-CH$_3$ | " | 84–86 |
| " | O | 4-OCHF$_2$ | " | |
| " | O | 3-OCF$_2$CHFCl | " | |
| " | O | 4-S—C$_4$H$_9$ | " | |
| —CH$_2$—CH$_2$—CH(CH$_3$)— | O | 4-Cl | " | |
| —(CH$_2$)$_3$— | O | 3-F | " | 72–74 |
| " | O | 4-F | " | |
| " | O | 2-F | " | |
| " | O | 4-I | " | |
| —CH(CH$_3$)CH$_2$CH$_2$— | O | 4-Cl | " | 109–111 |
| —(CH$_2$)$_3$— | O | 4-CH$_3$ | H | 197–200 |
| " | O | 3-Cl | H | 149–150 |
| " | O | 4-Cl | C$_2$H$_5$ | 98–99 |
| " | O | 4-Cl | C$_3$H$_7$ | |
| " | O | 4-Cl | i-C$_3$H$_7$ | |
| " | O | 4-Cl | C$_4$H$_9$ | |
| " | O | 4-Cl | t-C$_4$H$_9$ | |
| —CH(CH$_3$)CH$_2$— | — | H | CH$_3$ | 83–85 |
| —(CH$_2$)$_3$— | O | 2,4-Cl$_2$ | " | 118–120 |
| —CH$_2$— | O | 2-CH$_3$, 4-Cl | " | 120–122 |
| —(CH$_2$)$_3$— | O | 2-CH$_3$, 4-Cl | " | 134–138 |
| —(CH$_2$)$_4$— | O | H | " | 98–100 |
| " | O | 2-CH$_3$ | " | 69–71 |
| " | O | 2-CH$_3$, 4-Cl | " | 74–76 |
| " | O | 2,4-Cl$_2$ | " | 74–76 |
| " | O | 3,4-Cl$_2$ | " | 80–82 |
| —(CH$_2$)$_3$— | — | 4-OCH$_3$ | " | 79–81 |
| —(CH$_2$)$_4$— | O | 2,4,5-Cl$_3$ | " | |
| —CH$_2$— | O | 4-NO$_2$ | " | |
| " | — | 3-CH$_3$ | " | 95–96 |
| —C(CH$_3$)$_2$— | O | 2-CH$_3$ | " | |
| —(CH$_2$)$_2$— | O | H | " | 98–101 |
| —CH(CH$_3$)CH$_2$— | — | 4-NO$_2$ | " | 132–135 |
| —C(CH$_3$)$_2$— | — | 4-CH$_3$ | " | 132–135 |
| —CH(C$_2$H$_5$)— | — | H | " | 99–100 |
| —(CH$_2$)$_6$— | — | H | " | |
| " | O | H | " | |
| —CH$_2$— | S | 4-Cl | " | |

| A | $Z_n$ | $X_m$ | $R^1$ | Mp [°C] |
|---|---|---|---|---|
| —(CH$_2$)$_3$— | O | α-naphthyl | CH$_3$ | 108–110 |
| " | O | β-naphthyl | " | 114–116 |
| " | O | α-naphthyl | H | |
| " | O | 6-methyl-α-naphthyl | CH$_3$ | |
| " | O | 4,6-dimethyl-α-naphthyl | CH$_3$ | |
| " | O | β-naphthyl | H | 176–178 |

The Examples which follow illustrate the preparation of the herbicidal thiadiazole derivatives of the formula I.

EXAMPLE 1

6.5 g of propionyl chloride were added, at 20° C., to a mixture of 15 g of 2-(3-phenylpropyl)-5-amino-1,3,4-thiadiazole, 8.4 g of sodium bicarbonate and 200 g of tetrahydrofuran, the mixture was stirred for 12 hours at 20° C., filtered and evaporated down, and the residue was then stirred with petroleum ether. A white substance of melting point 167°–169° C. and of the following structural formula was obtained:

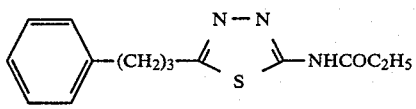

EXAMPLE 2

A mixture of 15 g of 2-[3-(4'-chlorophenoxy)propyl]-5-methylamino-1,3,4-thiadiazole, 3 g of methyl isocyanate, 2 drops of dibutyl-tin diacetate and 200 g of tetrahydrofuran was refluxed for 4 hours and then evaporated down, the residue was triturated with diethyl ether and the product was filtered off under suction. A white substance of melting point 83°–85° C. and of the following formula was obtained:

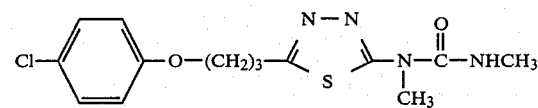

The thiadiazole derivatives below can be or may be prepared in a similar manner:

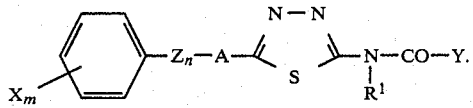

| No. | Y | R¹ | $-Z_n-A-$ | $X_m$ | M.p. [°C.] |
|---|---|---|---|---|---|
| 3 | NHCH₃ | CH₃ | —O—CH₂— | 4-Cl | 146–149 |
| 4 | " | " | —CH₂— | 4-phenyl | 152–154 |
| 5 | " | " | —O—(CH₂)₄— | 4-Cl | 82–84 |
| 6 | " | " | —O—(CH₂)₂— | 4-Cl | 95–97 |
| 7 | " | " | —(CH₂)₃— | H | 136–138 |
| 8 | " | " | —(CH₂)₂— | H | 152–154 |
| 9 | " | " | —O—CH(CH₃)CH₂CH₂— | 4-Cl | 72–75 |
| 10 | " | " | —O—CH₂CH₂CH(CH₃)— | 4-Cl | |
| 11 | " | " | —S—(CH₂)₃— | 4-Cl | |
| 12 | " | " | —O—(CH₂)₃— | 2-CH₃ | 120–123 |
| 13 | " | " | " | 3-CH₃ | 73–75 |
| 14 | " | " | " | 4-CH₃ | 106–108 |
| 15 | " | " | " | 2-CH₃, 4-Cl | 107–109 |
| 16 | " | " | " | 2,4-Cl₂ | 125–127 |
| 17 | " | " | " | 2,4,5-Cl₃ | |
| 18 | " | " | " | 3,4-Cl₂ | 127–129 |
| 19 | " | " | " | 3,5-Cl₂ | 150–152 |
| 20 | " | " | " | 2-Cl | 133–135 |
| 21 | " | " | " | 3-Cl | 140–142 |
| 22 | " | " | " | 4-NO₂ | 172–174 |
| 23 | " | " | " | 4-CN | 169–171 |
| 24 | " | " | " | 4-Br | 137–139 |
| 25 | " | " | —O(CH₂)₃— | 3-F | |
| 26 | " | " | " | 4-F | |
| 27 | " | " | " | 4-SCH₃ | |
| 28 | " | " | " | 4-SO₂CH₃ | |
| 29 | " | " | " | 4-OCH₃ | 112–114 |
| 30 | " | " | " | 3-OC₂H₅ | |
| 31 | " | " | " | H | 114–115 |
| 32 | " | " | " | 4-t-C₄H₉ | 132–133 |
| 33 | " | " | " | 4-C₂H₅ | 80–82 |
| 34 | " | " | " | 4-CF₃ | |
| 35 | " | " | " | 3-CF₃ | 100–102 |
| 40 | " | " | " | 4-cyclopentyl | |
| 41 | " | " | " | 4-cyclohexyl | |
| 42 | " | " | " | 4-(4'-chlorophenoxy) | |
| 43 | " | " | " | 4-(2',4'-dichlorophenoxy) | |
| 44 | " | " | " | 4-OCHF₂ | |
| 45 | " | " | " | 3-OCF₂CHFCl | |
| 46 | " | " | " | 4-SC₄H₉ | |
| 47 | " | " | " | 3-NO₂ | |
| 48 | " | H | —OCH₂— | 4-Cl | 251–253 |
| 49 | " | " | —CH₂— | 4-phenyl | 240–245 |
| 50 | " | " | —O(CH₂)₄— | 4-Cl | 186–188 |
| 51 | " | " | —O—(CH₂)₃— | 4-Cl | 175–177 |
| 52 | " | " | —O—(CH₂)₂— | 4-Cl | |
| 53 | " | " | —(CH₂)₃— | H | 174–176 |
| 54 | " | " | —(CH₂)₂— | H | 162–165 |
| 55 | " | " | —O—(CH₂)₃— | 3-CH₃ | 147–148 |
| 56 | " | " | " | 4-CH₃ | 172–174 |
| 57 | " | " | " | 3-Cl | 143–144 |
| 58 | " | " | " | 2-CH₃, 4-Cl | |

-continued

| No. | Y | R¹ | —Z$_n$—A— | X$_m$ | M.p. [°C.] |
|---|---|---|---|---|---|
| 59 | " | " | " | 2,4-Cl$_2$ | |
| 60 | " | " | " | 2,4,5-Cl$_3$ | |
| 62 | " | " | —OCH(CH$_3$)CH$_2$CH$_2$— | 4-Cl | |
| 63 | " | " | —OCH$_2$CH$_2$CH(CH$_3$)— | 4-Cl | |
| 64 | N(OCH$_3$)CH$_3$ | " | " | 4-Cl | |
| 65 | " | " | —O(CH$_2$)$_3$— | 4-Cl | 117–119 |
| 66 | " | " | " | 4-CH$_3$ | |
| 67 | " | " | " | 3-Cl | |
| 68 | " | " | " | 4-CH$_3$ | |
| 69 | " | " | —O—(CH$_2$)$_4$— | 4-Cl | 109–111 |
| 70 | " | " | —(CH$_2$)$_3$— | H | oil |
| 71 | " | " | —(CH$_2$)$_2$— | H | 96–98 |
| 72 | " | " | —OCH$_2$— | 4-Cl | 159–161 |
| 73 | C$_2$H$_5$ | " | " | 4-Cl | 223–225 |
| 74 | N(OCH$_3$)CH$_3$ | CH$_3$ | —O—(CH$_2$)$_4$— | 4-Cl | 86–88 |
| 75 | " | " | —(CH$_2$)$_3$— | H | oil |
| 76 | " | " | —(CH$_2$)$_2$— | H | oil |
| 77 | " | " | —OCH$_2$— | 4-Cl | 103–105 |
| 78 | " | " | —O(CH$_2$)$_3$— | 2-Br, 4-Cl | |
| 79 | " | " | " | 2,4-Cl$_2$ | |
| 80 | " | " | " | 3-Cl | |
| 81 | " | " | " | 2-CH$_3$, 4-Cl | |
| 82 | " | " | " | 3-CH$_3$ | |
| 83 | " | " | " | 4-CH$_3$ | |
| 84 | " | " | " | 3-F | |
| 85 | C$_2$H$_5$ | " | " | 4-Cl | 112–114 |
| 86 | " | " | —O(CH$_2$)$_4$— | 4-Cl | 102–104 |
| 87 | " | " | —CH$_2$— | 4-phenyl | 115–117 |
| 88 | " | " | —OCH$_2$— | 4-Cl | 118–120 |
| 89 | " | " | —(CH$_2$)$_3$— | H | 75–77 |
| 90 | " | " | —(CH$_2$)$_2$— | H | 79–81 |
| 91 | " | H | " | H | 172–175 |
| 92 | " | " | —O(CH$_2$)$_3$— | 4-Cl | |
| 93 | " | " | —O(CH$_2$)$_4$— | 4-Cl | 198–200 |
| 94 | " | " | —CH$_2$— | 4-phenyl | 231–233 |
| 95 | cyclopropyl | " | —O(CH$_2$)$_3$— | 4-Cl | |
| 96 | C$_3$H$_7$ | " | —O—(CH$_2$)$_3$— | 4-Cl | |
| 97 | t-C$_4$H$_9$ | " | " | 4-Cl | |
| 98 | sec-C$_4$H$_9$ | " | " | 4-Cl | |
| 99 | SCH$_3$ | " | " | 4-Cl | |
| 100 | OCH$_3$ | " | " | " | |
| 101 | SC$_2$H$_5$ | " | " | " | |
| 102 | OC$_2$H$_5$ | " | " | " | |
| 103 | O—i-C$_3$H$_7$ | " | " | " | |
| 104 | N(CH$_3$)$_2$ | " | " | " | |
| 105 | NHC$_2$H$_5$ | " | " | " | |
| 106 | N(CH$_3$)C$_4$H$_9$ | " | " | " | |
| 107 | N(CH$_3$)CH(CH$_3$)C≡CH | " | " | " | |
| 108 | N(OC$_2$H$_5$)CH$_3$ | " | " | " | |
| 109 | N(OC$_3$H$_7$)C$_3$H$_7$ | " | " | " | |
| 110 | morpholino | " | " | " | |
| 111 | piperidino | " | " | " | |
| 112 | pyrrolidino | " | " | " | |
| 113 | isoxazolidino | " | " | " | |
| 114 | 1,2-oxazinano | " | " | " | |

-continued

| No. | Y | R¹ | —$Z_n$—A— | $X_m$ | M.p. [°C.] |
|---|---|---|---|---|---|
| 115 | 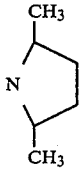 | " | " | " | |
| 116 | $NHC_2H_5$ | $CH_3$ | " | " | 113–116 |
| 117 | $NHC_3H_7$ | " | " | " | |
| 118 | $NHcycC_3H_5$ | " | " | " | |
| 119 | $NHCH_2CH=CH_2$ | " | " | " | |
| 120 | $NHCH_2C\equiv CH$ | " | " | " | |
| 121 | $NHCH_2CH_2OCH_3$ | " | " | " | |
| 122 | cyclopentylamino | " | " | " | |
| 123 | $NHCH_3$ | $C_2H_5$ | " | " | 120–122 |
| 124 | $NHCH_3$ | $t-C_4H_9$ | " | " | |
| 125 | $NHCH_3$ | $CH_3$ | " | 4-I | |
| 126 | " | " | —$CH(CH_3)CH_2$— | H | |
| 127 | " | " | —$OCH_2$— | 2-$CH_3$, 4-Cl | 186–188 |
| 128 | " | " | " | 4-$NO_2$ | |
| 129 | " | " | —$SCH_2$— | 4-Cl | |
| 130 | " | " | —$OCH_2$— | 2,4-$Cl_2$ | |
| 131 | " | " | —$OCH(CH_3)$— | 2,4-$Cl_2$ | |
| 132 | " | " | —$OCH(CH_3)$— | 4-(2′,4′-dichlorophenoxy) | |
| 133 | " | " | —$O(CH_2)_4$— | H | 87–89 |
| 134 | " | " | " | 2-$CH_3$ | 112–114 |
| 135 | " | " | " | 2-$CH_3$, 4-Cl | 116–118 |
| 136 | " | " | " | 2,4-$Cl_2$ | 127–129 |
| 137 | " | " | " | 3,4-$Cl_2$ | 98–100 |
| 138 | " | " | —$(CH_2)_3$— | 4-$OCH_3$ | 87–88 |
| 139 | " | " | —$O(CH_2)_4$— | 2,4,5-$Cl_3$ | |
| 140 | " | " | —$CH_2$— | 3-$CH_3$ | 166–168 |
| 141 | " | " | —$OC(CH_3)_2$— | 2-$CH_3$ | |
| 142 | " | " | —$O(CH_2)_2$— | H | 168–170 |
| 143 | " | " | —$CH(CH_3)CH_2$— | 4-$NO_2$ | 153–155 |
| 144 | " | " | —$(CH_2)_6$— | H | |
| 145 | " | " | —$O(CH_2)_6$— | H | |
| 146 | " | " | —$SCH_2$— | H | |
| 147 | " | " | —$OCH(CH_3)$— | 3-$t-C_4H_9$ | |
| 148 | " | " | —$OCH(CH_3)$— | 2,4,5-$Cl_3$ | |
| 149 | " | " | —$OCH(CH_3)$— | 2-$CH_3$, 4,5-$Cl_2$ | |
| 150 | " | " | —$O(CH_2)_7$— | 4-Cl | |
| 151 | $OCH_3$ | H | —$(CH_2)_3$— | H | 178–180 |
| 152 | $SCH_3$ | $CH_3$ | —$OCH_2$— | 4-Cl | 108–110 |
| 153 | $OCH_3$ | " | " | " | 114–116 |
| 154 | $NHCH_3$ | " | —$C(CH_3)_2CH_2$— | 4-$CH_3$ | 127–130 |
| 155 | " | " | " | H | 133–135 |
| 156 | " | " | —$CH(C_2H_5)$— | H | 124–125 |
| 157 | " | H | —$O(CH_2)_3$— | 4-$OCH_3$ | 137–138 |
| 158 | " | " | " | 4-Br | 162–163 |
| 159 | " | " | " | 2-Cl | 175–177 |
| 160 | " | " | " | 4-$C_2H_5$ | 165–167 |
| 161 | " | " | " | 3-F | 140–141 |
| 162 | " | $CH_3$ | —$O(CH_2)_2$— | 4-$t-C_4H_9$ | 119–121 |
| 167 | $C_2H_5$ | H | —$O(CH_2)_3$— | 3-$CH_3$ | 148–150 |
| 168 | " | " | " | 4-$t-C_4H_9$ | 156–158 |
| 169 | " | " | " | 4-CN | 225–230 |
| 170 | " | " | " | 2-Cl | 162–163 |
| 171 | " | " | " | 3,4-$Cl_2$ | 170–172 |
| 172 | " | " | " | 3,5-$Cl_2$ | 193–195 |
| 173 | $NHCH_3$ | $CH_3$ | —$(CH_2)_4$— | H | 123–125 |
| 174 | " | " | " | 4-$CH_3$ | 98–100 |
| 175 | " | " | " | 4-$OCH_3$ | 120–122 |
| 176 | " | " | " | 4-Cl | 89–91 |
| 177 | " | " | " | 3,4-$Cl_2$ | |
| 178 | " | " | —$(CH_2)_5$— | 4-$CH_3$ | oil |
| 179 | " | " | " | 4-Cl | |
| 180 | " | " | —$O(CH_2)_4$— | 3-$CH_3$ | 102–104 |
| 182 | " | " | " | 2-Cl | 81–83 |
| 183 | " | " | " | 3,5-$Cl_2$ | 134–136 |
| 184 | " | " | " | 2,5-$Cl_2$ | 115–117 |
| 185 | " | " | " | 3-Br | 105–107 |
| 186 | " | " | " | 3,5-$(CH_3)_2$ | 139–141 |
| 187 | " | " | " | 3-Cl | 87–89 |
| 188 | " | " | " | 4-Br | 105–106 |
| 189 | " | " | " | 3,4-$(CH_3)_2$ | 111–113 |
| 190 | " | H | " | 2-$CH_3$ | 136–137 |
| 191 | " | $CH_3$ | —$OCH_2$— | 2,4-$Cl_2$ | 173–176 |
| 192 | " | " | —$O(CH_2)_5$— | 3,4-$Cl_2$ | 108–110 |

-continued

| No. | Y | R¹ | —Zₙ—A— | Xₘ | M.p. [°C.] |
|---|---|---|---|---|---|
| 193 | " | H | —O(CH₂)₄— | 3-CH₃ | 67–68 |
| 194 | CH₃ | CH₃ | " | 3,4-Cl₂ | 106–108 |
| 195 | C₂H₅ | " | " | 3,4-Cl₂ | 102–104 |
| 196 | CH₃ | " | —CH₂— | 3-CH₃ | 78–79 |
| 197 | C₂H₅ | " | " | 3-CH₃ | 77–78 |
| 198 | NHCH₃ | " | " | 4-Cl | 197–199 |
| 199 | " | " | " | 4-OCH₃ | 175–177 |
| 200 | " | " | " | 4-CH₃ | 202–203 |
| 201 | " | " | " | H | 188–190 |
| 202 | " | " | " | 2-OCH₃ | 208–209 |
| 203 | " | " | " | 2-Cl | 204–206 |
| 204 | " | " | " | 2,4-Cl₂ | 160–162 |
| 205 | " | " | " | 3-CF₃ | 119–121 |
| 206 | " | " | " | 3-OCH₃ | 138–140 |
| 207 | N(OCH₃)CH₃ | " | " | 3-CH₃ | 70–72 |
| 208 | NH(n-C₄H₉) | " | " | 3-CH₃ | 91–93 |
| 209 | NH(n-C₄H₉) | " | —O(CH₂)₃— | 4-Cl | 82–85 |
| 210 | NH(CH₂OCH₃) | " | " | 4-Cl | 86–88 |
| 211 | NH(t-C₄H₉) | " | " | 4-Cl | 98–100 |
| 212 | N(OCH₃)CH₃ | " | " | 4-Cl | 106–108 |
| 213 | NH(C(CH₃)₂C≡CH) | " | " | 4-Cl | 88–91 |
| 214 | NHCH₃ | CH₃ | —CH₂CH(CH₃)— | 4-t-C₄H₉ | 113–114 |
| 215 | NHCH₃ | C₂H₅ | —O(CH₂)₄— | 2-CH₃ | 89–90 |
| 216 | NHCH₃ | C₂H₅ | " | H | 92–94 |
| 217 | NHCH₃ | C₂H₅ | " | 3,4-Cl₂ | 75–78 |
| 218 | NHCH₃ | H | " | 3,4-Cl₂ | 177–178 |
| 219 | NHCH₃ | CH₃ | —SCH₂— | 2,5-(CH₃)₂, 4-Cl | 173–174 |
| 220 | NHCH₃ | CH₃ | —OCH(CH₃) | 2-CH₃, 4-Cl | 47–48 |

| No. | Y | R¹ | —Zₙ—A— | Xₘ | M.p. [°C.] |
|---|---|---|---|---|---|
| 36 | NHCH₃ | CH₃ | —O—(CH₂)₃— | α-naphthyl | 100–102 |
| 37 | NHCH₃ | " | " | β-naphthyl | 112–114 |
| 38 | NHCH₃ | " | " | 2-methyl-α-naphthyl | |
| 39 | NHCH₃ | " | " | 2,4-dimethyl-α-naphthyl | |
| 61 | NHCH₃ | H | " | 4-chloro-α-naphthyl | |
| 163 | NHCH₃ | H | " | α-naphthyl | |
| 164 | NHCH₃ | H | " | β-naphthyl | |
| 165 | C₂H₅ | H | " | α-naphthyl | >240 |
| 166 | C₂H₅ | H | " | β-naphthyl | 162–164 |
| 181 | NHCH₃ | CH₃ | —O—(CH₂)₄— | α-naphthyl | 110–112 |

Compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound 1 is mixed with 10 parts by weight of N-methyl-alpha-pyrrolidone. A mixture is obtained which is suitable for application in the form of very fine drops.

II. 20 parts by weight of compound no. 3 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 8 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 7 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 6 is intimately mixed with 97 parts by weight of particulate kaolin. A dust is obtained containing 3% by weight of the active ingredient.

VII. 30 parts by weight of compound no. 51 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 1 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved and the growth stage of the plants, and varies from 0.05 to 10 kg/ha and more, but is preferably from 0.1 to 5 kg/ha.

The herbicidal action of compounds of the formula I is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. The soybean plants used for the postemergence treatment were grown in a peat-enriched substrate. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were 0.125, 0.25, 0.5, 1.0 and 3.0 kg of active ingredient per hectare.

The pots were set up on the greenhouse—species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Amaranthus spp., *Amaranthus retroflexus, Avena sativa, Beta vulgaris, Cassia tora, Centaurea cyanus, Chenopodium album, Euphorbia geniculata, Galium aparine,* Glycine max., *Gossypium hirsutum,* Ipomoea spp., Lamium spp., *Lolium multiflorum,* Setaria spp., *Sinapis alba, Solanum nigrum, Triticum aestivum, Veronica persica, Viola tricolor,* Zea mays, and *Oryza sativa*.

On preemergence application in the greenhouse, compounds nos. 7, 9, 25, 31 and 156, at 3.0 kg/ha, had a considerable herbicidal action.

On postemergence application of 3.0 kg/ha, compounds nos. 3, 4, 5, 6, 7, 51, 53, 54, 69, 89, 94 and 152 had a good herbicidal action on the plants tested. Compound no. 2, on postemergence application of 0.25 kg/ha, had a very good herbicidal action on numerous broadleaved unwanted plants.

On postemergence application, compounds nos. 9, 69, and 152, at 0.5 kg/ha, selectively combated unwanted plants in crops. Broadleaved weeds in Indian corn were combated with a post-emergence application of 0.125 kg/ha of compound no. 35. Further, compound no. 18 at 0.25 kg/ha and compounds nos. 32 and 37 at 1.0 kg/ha had a selective action on weeds.

In view of the many application methods possible, the compounds according to the invention may be used in a large number of crop plants for removing unwanted plant growth.

The following crop plants may be mentioned by way of example:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Brassica napus var. napobrassica | |
| Brassica napus var. rapa | turnips |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A thiadiazole derivative of the formula

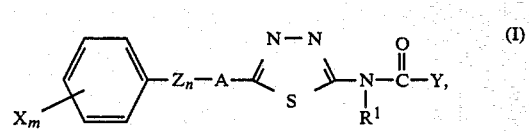

where $R^1$ is hydrogen or $C_1$-$C_4$-alkyl, A is an alkylene chain of 1 to 8 carbon atoms which is unsubstituted or substituted by $C_1$-$C_4$-alkyl, X is hydrogen, halogen, cyano, nitro, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylthio, $C_1$-$C_4$-alkylsulfonyl, $C_3$-$C_6$-cycloalkyl, phenyl, or unsubstituted or halogen-substituted aryloxy, m is 0, 1, 2, 3 or 4, Y is $C_1$-$C_4$-alkyl, $C_3$-$C_6$-cycloalkyl or $NR^2R^3$, where $R^2$ and $R^3$ independently of one another are each hydrogen, $C_1$-$C_4$-alkyl, $C_2$-$C_4$-alkenyl, $C_2$-$C_4$-alkynyl, $C_1$-$C_4$-alkoxy or $C_3$-$C_6$-cycloalkyl, Z is oxygen or sulfur and n is 1, and where the radical

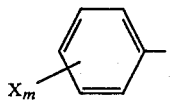

may be replaced by naphthyl which is unsubstituted or substituted by halogen, $C_1$–$C_4$-alkyl or $C_1$–$C_4$-alkoxy.

2. A thiadiazole of the formula I as defined in claim 1, wherein n is 1 and Y is $NR^2R^3$.

3. N-[2-[3-(4'-Chlorophenoxy)-propyl]-1,3,4-thiadiazol-5-yl]-N-methyl-N'-methylurea.

4. A herbicide containing inert additives and an effective amount of a thiadiazole derivative of the formula I as claimed in claim 1.

5. A herbicide containing inert additives and an effective amount of N-[2-[3-(4'-chlorophenoxy)-propyl]-1,3,4-thiadiazol-5-yl]-N-methyl-N'-methylurea.

6. A process for combating unwanted plant growth, wherein a herbicidally effective amount of a thiadiazole derivative of the formula I as claimed in claim 1 is allowed to act on the plants and/or their location.

7. A thiadiazole of the formula

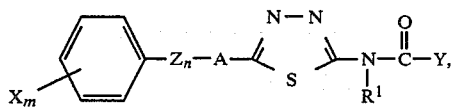

where $R^1$ is $C_1$–$C_4$-alkyl, A is an alkylene chain of 1 to 8 carbon atoms which is unsubstituted or substituted by $C_1$–$C_4$-alkyl, X is hydrogen, halogen, cyano, nitro, $C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio, $C_1$–$C_4$-alkylsulfonyl, $C_3$–$C_6$-cycloalkyl, phenyl, or unsubstituted or halogen-substituted aryloxy, m is 0, 1, 2, 3 or 4, Y is $NR^2R^3$, where $R^2$ is hydrogen and $R^3$ is $C_1$–$C_4$-alkyl, Z is oxygen or sulfur and n is 0 or 1, and where the radical

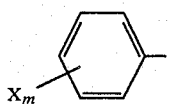

may be replaced by naphthyl which is unsubstituted or substituted by halogen, $C_1$–$C_4$-alkyl or $C_1$–$C_4$-alkoxy.

8. A herbicide containing inert additives and an effective amount of a thiadiazole derivative of the formula I as claimed in claim 7.

9. A thiadiazole derivative of the formula I as claimed in claim 8, where $R^1$ is methyl and Y is $NR^2R^3$, $R^2$ denoting hydrogen and $R^3$ methyl.

10. A process for combating unwanted plant growth, wherein a herbicidally effective amount of a thiadiazole derivative of the formula I as set forth in claim 7 is allowed to act on the plants and/or their location.

11. A herbicide containing inert additives and an effective amount of a thiadiazole derivative of the formula I as claimed in claim 8, where $R^1$ is methyl and Y is $NR^2R^3$, $R^2$ denoting hydrogen and $R^3$ methyl.

* * * * *